(12) United States Patent
Kracker

(10) Patent No.: US 8,849,385 B2
(45) Date of Patent: *Sep. 30, 2014

(54) LEAD INTEGRITY TESTING DURING SUSPECTED TACHYARRHYTHMIAS

(75) Inventor: Stefan G. Kracker, Sonthofen (DE)

(73) Assignee: Medtronic, Inc., Minneapolis, MN (US)

( * ) Notice: Subject to any disclaimer, the term of this patent is extended or adjusted under 35 U.S.C. 154(b) by 638 days.

This patent is subject to a terminal disclaimer.

(21) Appl. No.: 13/116,042

(22) Filed: May 26, 2011

(65) Prior Publication Data

US 2011/0224566 A1  Sep. 15, 2011

Related U.S. Application Data

(63) Continuation of application No. 12/164,583, filed on Jun. 30, 2008, now Pat. No. 7,974,690.

(51) Int. Cl.
  *A61B 5/0424* (2006.01)
  *A61B 5/0464* (2006.01)
  *A61N 1/39* (2006.01)
  *A61N 1/37* (2006.01)
  *G06F 19/00* (2011.01)
  *A61N 1/08* (2006.01)

(52) U.S. Cl.
  CPC ............ *A61N 1/3706* (2013.01); *A61N 1/3925* (2013.01); *A61N 2001/083* (2013.01); *G06F 19/3412* (2013.01)
  USPC .......................................... 600/518; 600/547

(58) Field of Classification Search
  None
  See application file for complete search history.

(56) References Cited

U.S. PATENT DOCUMENTS 7,974,690 B2 * 7/2011 Kracker ............................ 607/6
2005/0096708 A1 * 5/2005 Seim et al. ....................... 607/28

* cited by examiner

*Primary Examiner* — Kennedy Schaetzle
(74) *Attorney, Agent, or Firm* — Michael J. Ostrom; Stephen W. Bauer

(57) ABSTRACT

Techniques for performing a lead integrity test during a suspected tachyarrhythmia are described. An implantable medical device (IMD) may perform the test prior to delivering a therapeutic shock to treat the suspected tachyarrhythmia and, in some cases, may withhold the shock based on the test. In some examples, the IMD measures an impedance of a lead a plurality of times during the suspected tachyarrhythmia. In some examples, the IMD measures the impedance a plurality of times between two sensed events of the suspected tachyarrhythmia. The IMD or another device may determine a variability of, or otherwise compare, the measured impedances to evaluate the integrity of the lead. Instead of or in addition to withholding a shock, the IMD or another device may change a sensing or stimulation vector of the IMD, or provide an alert to a user, if the integrity test indicates a possible lead integrity issue.

15 Claims, 11 Drawing Sheets

LEAD INTEGRITY TESTING DURING SUSPECTED TACHYARRHYTHMIAS

This application is a continuation of U.S. application Ser. No. 12/164,583, filed Jun. 30, 2008, now U.S. Pat. No. 7,974,690, the entire content of which is incorporated herein by reference.

TECHNICAL FIELD

The disclosure relates to implantable medical devices, and, more particularly, to testing integrity of implantable medical device sensing components.

BACKGROUND

A variety of implantable medical devices for delivering a therapy and/or monitoring a physiological condition have been clinically implanted or proposed for clinical implantation in patients. Some implantable medical devices may employ one or more elongated electrical leads carrying stimulation electrodes, sense electrodes, and/or other sensors. Implantable medical devices may deliver electrical stimulation or fluid therapy and/or monitor conditions associated with the heart, muscle, nerve, brain, stomach or other organs or tissue.

Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry.

Implantable medical devices, such as cardiac pacemakers or implantable cardioverter-defibrillators, for example, provide therapeutic electrical stimulation to the heart via electrodes carried by one or more implantable leads. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting fibrillation.

Leads associated with an implantable medical device typically include a lead body containing one or more elongated electrical conductors that extend through the lead body from a connector assembly provided at a proximal lead end to one or more electrodes located at the distal lead end or elsewhere along the length of the lead body. The conductors connect stimulation and/or sensing circuitry within an associated implantable medical device housing to respective electrodes or sensors. Some electrodes may be used for both stimulation and sensing. Each electrical conductor is typically electrically isolated from other electrical conductors and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously disrupted. Connection mechanisms, such as set screws, may be insufficiently tightened at the time of implantation, followed by a gradual loosening of the connection. Also, lead pins may not be completely inserted. In some cases, changes in leads or connections may result in intermittent or continuous changes in lead impedance.

Short circuits, open circuits or significant changes in impedance may be referred to, in general, as lead related conditions. In the case of cardiac leads, sensing of an intrinsic heart rhythm through a lead can be altered by lead related conditions. Structural modifications to leads, conductors or electrodes may alter sensing integrity. Furthermore, impedance changes in the stimulation path due to lead related conditions may affect sensing and stimulation integrity for pacing, cardioversion, or defibrillation. In addition to lead related conditions, conditions associated with sensor devices or sensing circuitry, as well as conditions associated with electrodes or sensors not located on leads, may affect sensing integrity.

SUMMARY

In general, this disclosure is directed to techniques for performing a lead integrity test during a suspected tachyarrhythmia, such as a suspected tachycardia or fibrillation. The techniques may include performing the lead integrity test prior to delivering a shock or other therapy to treat the suspected tachyarrhythmia. A lead integrity test performed during a suspected tachyarrhythmia may indicate whether the suspected tachyarrhythmia was detected due to a lead integrity issue, rather than because a patient is experiencing an actual tachyarrhythmia. In some examples, if the integrity test indicates a possible integrity issue, an implantable medical device (IMD) may withhold the shock or other therapy, change a sensing or therapy configuration, and/or provide an alert. In some examples, if the integrity test indicates a possible integrity issue, the IMD may and attempt to change the sensing configuration and redetect the tachyarrhythmia to confirm that the tachyarrhythmia is indeed occurring before delivering a shock or other therapy.

In some examples, the IMD measures an impedance of a lead a plurality of times during the suspected tachyarrhythmia. In some examples, the IMD measures the impedance a plurality of times between two sensed events of the suspected tachyarrhythmia. The IMD or another device may determine a variability of, or otherwise compare, the measured impedances to evaluate the integrity of the lead. In general, rapid, intermittent fracture of a lead or disconnection of the lead from an IMD, which may be interpreted by the IMD as a plurality of sensed cardiac events, e.g., depolarizations, and lead to detection of a suspected tachyarrhythmia, may also result in variability of impedance measurements of the lead during the suspected tachyarrhythmia. Variability due to a lead integrity issue may be particularly evident in impedance measurements made between consecutive sensed events.

In some examples, the IMD also measures the impedance of the lead prior to detection the suspected tachyarrhythmia. For example, the IMD may periodically measure the impedance of the lead, such as one or more times of day at one or more particular times of day. The IMD may compare one or more of the impedances measured during the suspected tachyarrhythmia to such non-tachyarrhythmia impedances, and the evaluation of lead integrity may also be based on this comparison. When a lead integrity issue leads to detection of a suspected tachyarrhythmia, one or more impedances measured during the suspected tachyarrhythmia may differ significantly from the non-tachyarrhythmia impedances. Comparing impedances measured during a suspected tachyarrhythmia to at least one non-tachyarrhythmia impedance may include comparing a mean, median or other value derived from impedances measured during a suspected tachyarrhythmia to mean, median or other value derived from non-tachyarrhythmia impedances.

Furthermore, in some examples, a threshold for variability of impedance measurements made during a suspected tachyarrhythmia may be determined based on a variability of non-tachyarrhythmia impedances. Accordingly, in some examples, an IMD or other device determines a variability of non-tachyarrhythmia impedances, such as an overall variability of non-tachyarrhythmia impedances or the variability of the previous N non-tachyarrhythmia impedances. The IMD or other device may determine a threshold for variability of impedance measurements made during a suspected tachyarrhythmia by, for example, adding an offset to the variability of the non-tachyarrhythmia impedances. The offset may be, for example, an absolute numerical value or a percentage of the variability of the non-tachyarrhythmia impedances.

In one example, the disclosure provides a method comprising detecting a suspected tachyarrhythmia via at least one implantable medical lead, and in response to detecting the suspected tachyarrhythmia, measuring an impedance of the lead a plurality of times during the suspected tachyarrhythmia to obtain a plurality of impedance measurements. The method further comprises comparing the impedance measurements, and evaluating integrity of the lead based upon the comparison.

In another example, the disclosure provides a system that comprises an implantable medical lead, and an implantable medical device (IMD) coupled to the lead. The IMD detects a suspected tachyarrhythmia via the lead and, in response to detecting the suspected tachyarrhythmia, measures an impedance of the lead a plurality of times during the suspected tachyarrhythmia. The system further comprises a processor that compares the measured impedances, and evaluates integrity of the lead based upon the comparison.

In another example, the disclosure provides a computer-readable medium comprising instructions that cause a processor to detect a suspected tachyarrhythmia via at least one implantable medical lead, in response to detecting the suspected tachyarrhythmia, control measurement of an impedance of the lead a plurality of times during the suspected tachyarrhythmia to obtain a plurality of impedance measurements, compare the impedance measurements, and evaluate integrity of the lead based upon the comparison.

In another example, the disclosure provides a system comprising means for detecting a suspected tachyarrhythmia via at least one implantable medical lead, means for measuring an impedance of the lead a plurality of times during the suspected tachyarrhythmia to obtain a plurality of impedance measurements in response to detecting the suspected tachyarrhythmia, means for comparing the impedance measurements, and means for evaluating integrity of the lead based upon the comparison.

The details of one or more examples are set forth in the accompanying drawings and the description below. Other features, objects, and advantages of the disclosure will be apparent from the description and drawings, and from the claims.

DETAILED DESCRIPTION

As discussed above, this disclosure is generally directed to techniques for performing a lead integrity test during a suspected tachyarrhythmia, which may include performing the lead integrity test prior to delivering a shock or other therapy to treat the suspected tachyarrhythmia. In general, ventricular fibrillation and delivery of a responsive shock will be used as examples of a tachyarrhythmia and responsive therapy herein. However, the techniques described herein are not limited to use in conjunction with these examples. A suspected tachyarrhythmia may be a suspected atrial tachycardia, ventricular tachycardia, supraventricular tachycardia, atrial fibrillation, ventricular fibrillation, or any other tachyarrhythmia. A responsive therapy may be a defibrillation shock or pulse, cardioversion shock or pulse, one or more pacing pulses, such as anti-tachycardia pacing, or any other responsive therapy. The lead integrity test may be performed during a confirmation phase and/or charging phase prior to a responsive therapy delivery, and the test may be delivered in a manner such that it does not interfere with continuous cardiac signal detection or other functions. A detected tachyarrhythmia is referred to herein as "suspected," because the detection may be due to a lead integrity issue, rather than a true tachyarrhythmia of the heart of a patient.

Figure 1:
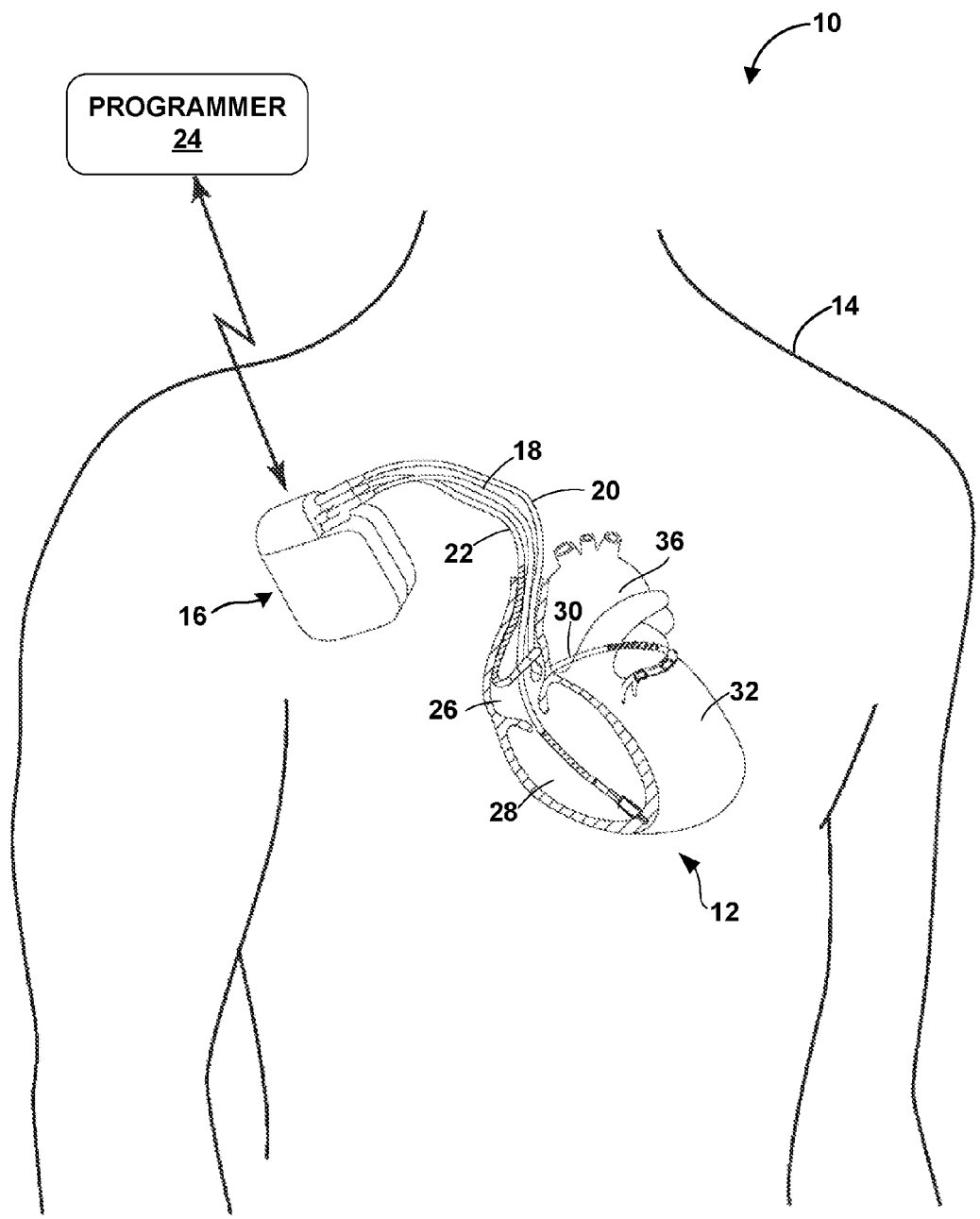
FIG. 1 is a conceptual drawing illustrating an example system that includes an implantable medical device (IMD) coupled to implantable medical leads.

FIG. 1 is a conceptual diagram illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily a human patient.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, therapy system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may include temporary or permanent epicardial or subcutaneous leads, instead of or in addition to leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art. As described herein, IMD 16 may also perform a lead integrity test during a suspected tachyarrhythmia, in order to evaluate the integrity of the sensing configuration that detected the tachyarrhythmia.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16. In some examples, this information may be presented to the user as an alert. For example, a lead integrity issue indicated by a lead integrity test may trigger IMD 16 to transmit an alert to the user via programmer 24.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
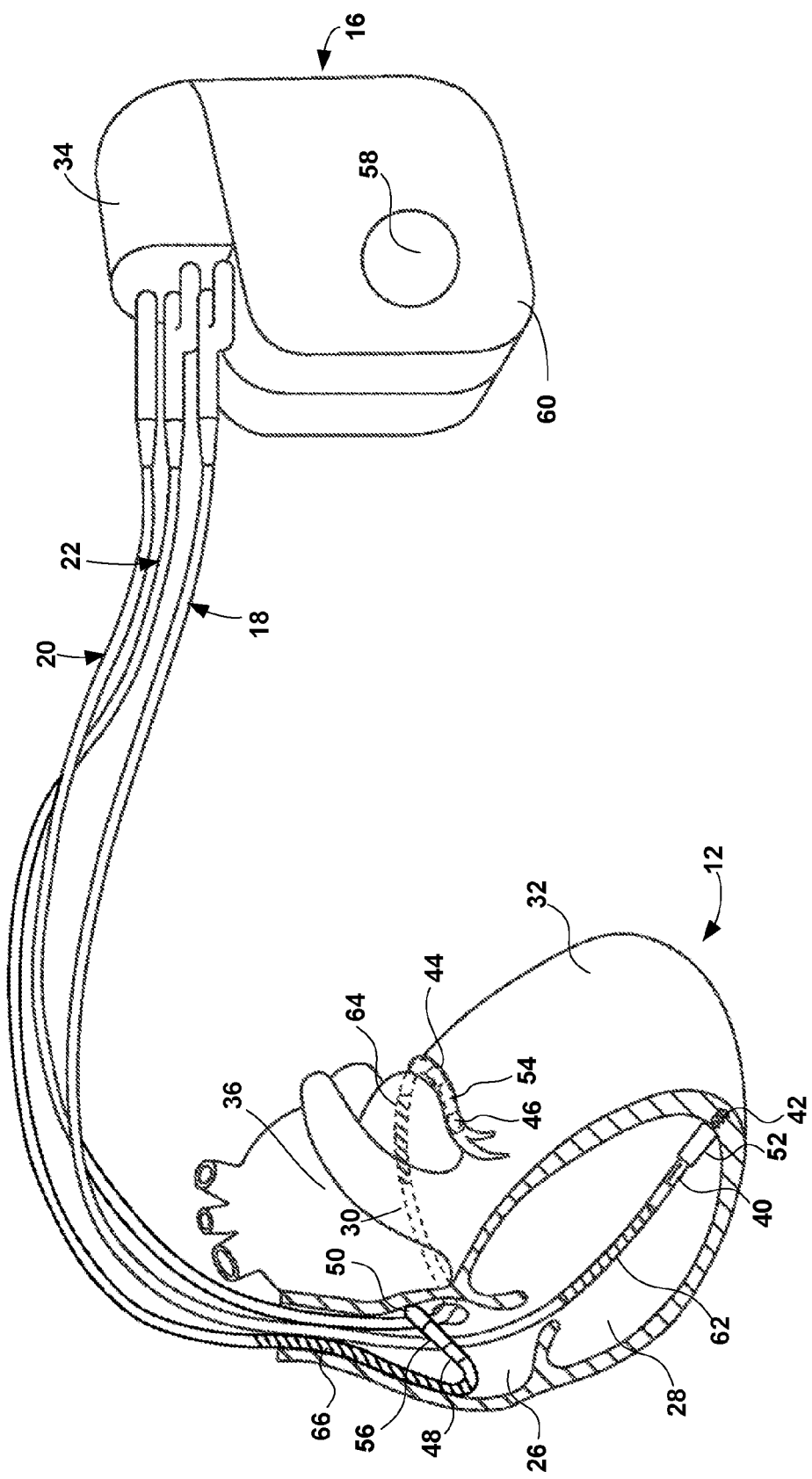
FIG. 2 is a conceptual drawing illustrating the example IMD and leads of FIG. 1 in conjunction with a heart.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58.

Any combination of electrodes 40, 42, 44, 46, 48, 50, 58, 62, 64 and 66 may be considered a sensing configuration that has one or more electrodes. In some examples, a sensing configuration may be a bipolar electrode combination on the same lead, such as electrodes 40 and 42 of lead 18. On one lead having three electrodes, there may be three different sensing configurations available to IMD 16. These sensing configurations are, for the example of lead 18, tip electrode 42 and ring electrode 40, tip electrode 42 and elongated electrode 62, and ring electrode 40 and elongated electrode 62. However, some embodiments may utilize sensing configurations having electrodes of two different leads. Furthermore, a sensing configuration may utilize housing electrode 58 as one of the electrodes. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
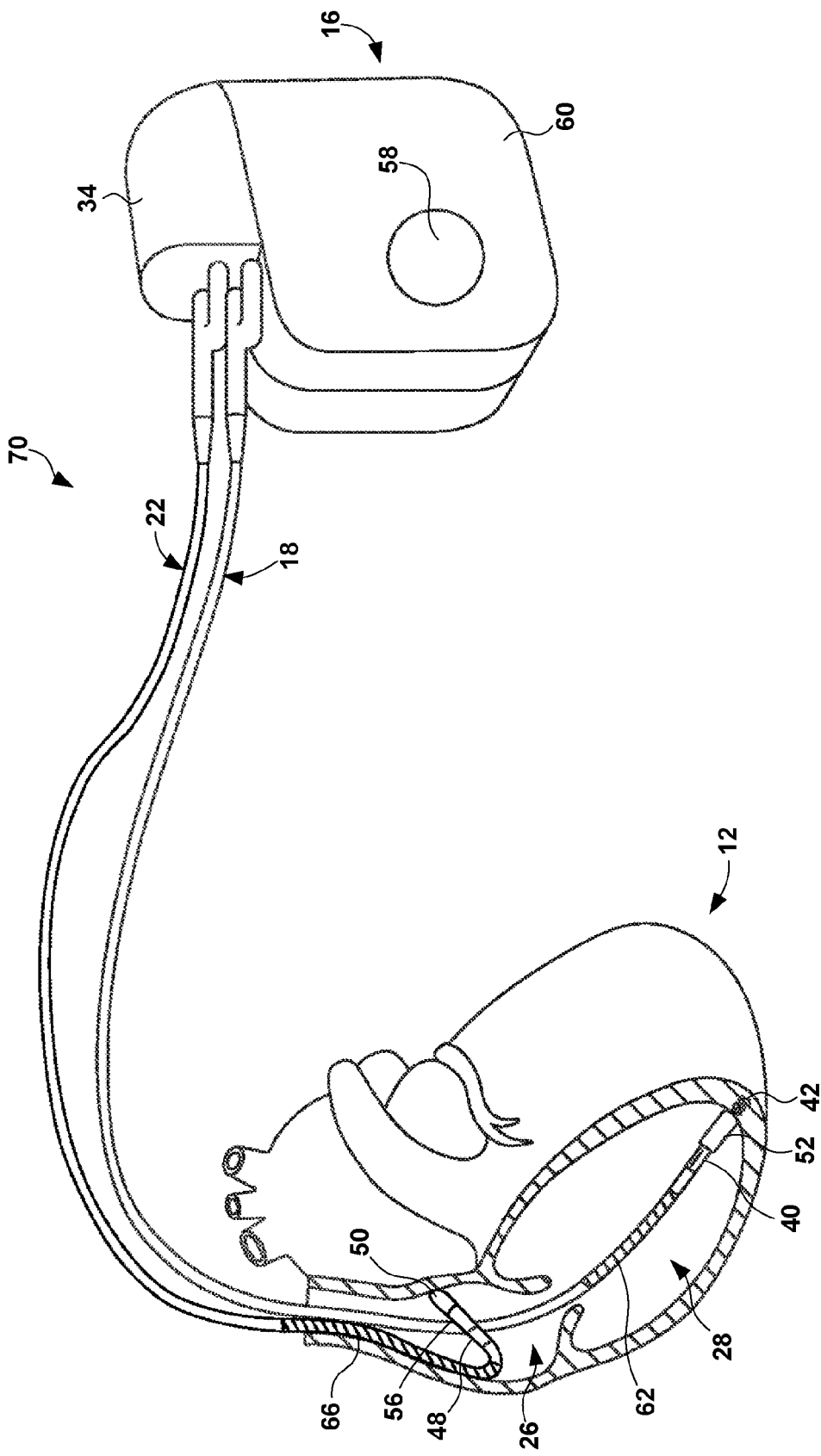
FIG. 3 is a conceptual drawing illustrating the example IMD of FIG. 1 coupled to a different configuration of implantable medical leads in conjunction with a heart.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used in sensing configurations that may be subject to a pre-shock integrity test.

FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Lead integrity testing according to this disclosure may be performed in two lead systems in the manner described herein with respect to three lead systems.

Figure 4:
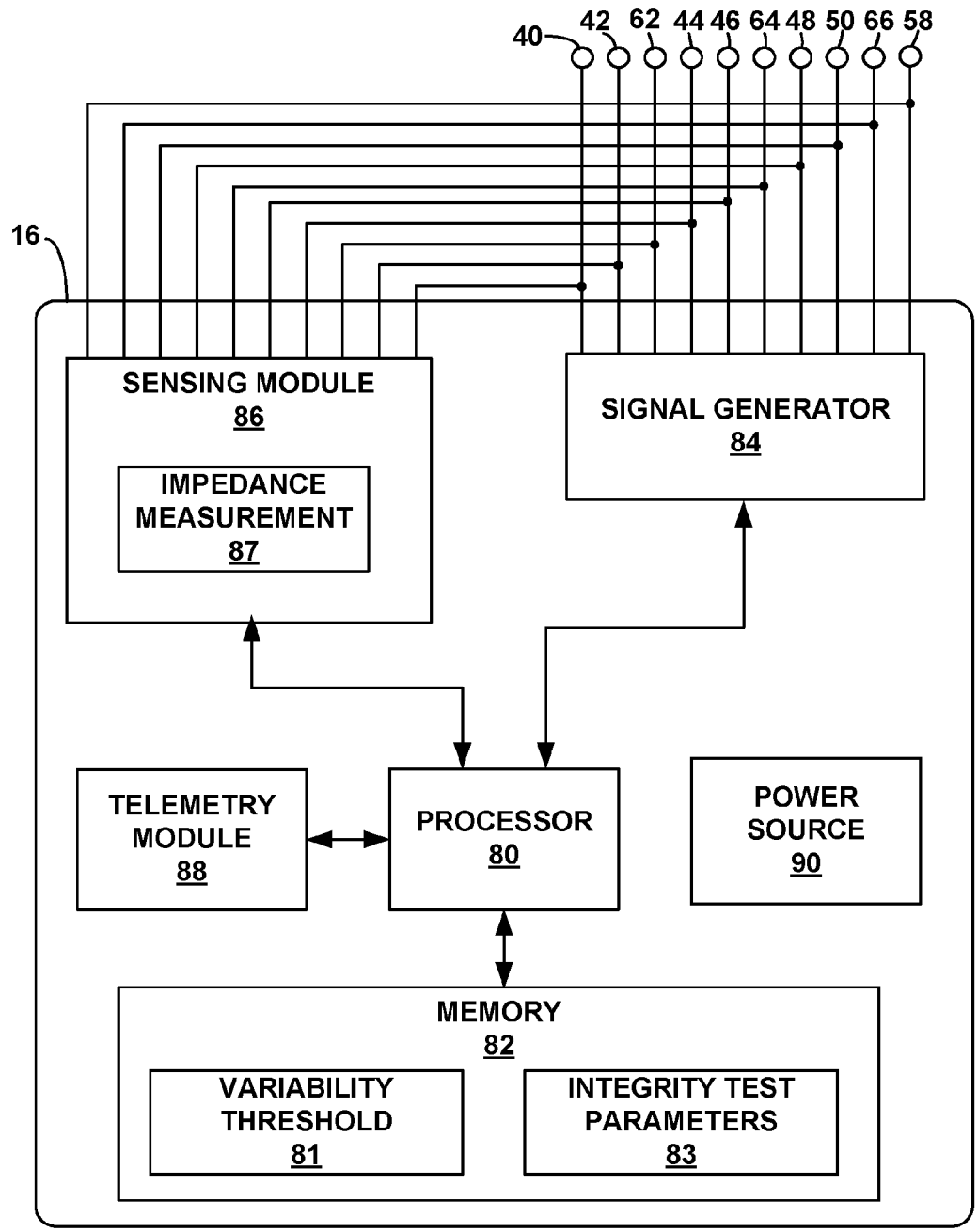
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense the cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, some various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 86 or processor 80. In some examples, processor 80 may store signals the digitized versions of signals from the wide band channel in memory 82 as electrograms (EGMs). In some examples, the storage of such EGMs in memory 82 may be under the control of a direct memory access circuit.

In some examples, processor 80 may employ digital signal analysis techniques to characterize the digitized signals from the wide band channel to, for example detect and classify the patient's heart rhythm. Processor 80 may detect and classify the patient's heart rhythm by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves with detection channels of sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by signal generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a suspected tachyarrhythmia event, such as ventricular fibrillation or ventricular tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver cardioversion or defibrillation pulses to heart 12, signal generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachycardia requiring a cardioversion or defibrillation pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of signal generator 84.

Rapid, intermittent fracture of one or more of leads 18, 20, 22 or disconnection of the lead from IMD 16 may be interpreted by the IMD 16 as a plurality of sensed cardiac events, e.g., R-waves, and result in detection of a suspected tachyarrhythmia by IMD 16. More particularly, "make/break" events resulting from intermittent fracture or disconnection of a conductor within a lead that is electrically connected to an electrode used in an electrode combination for a current sensing configuration may introduce noise into the signal received by a sensing channel of sensing module 86 that is electrically coupled to the electrode combination. An amplifier of the sensing channel may interpret such noise as events, e.g., R-waves, and provide indications of the events to processor 80. The rate of sensed events when such noise is present may be similar to or greater than that for detection of a tachyarrhythmia, and processor 80 may detect a tachyarrhythmia based the noise. Any tachyarrhythmia detected by processor 80 using any of the techniques described herein may be referred to as a suspected tachyarrhythmia, because the detection may be due to such noise, rather than an actual tachyarrhythmia of heart 12.

In response to detection of a suspected tachyarrhythmia, processor 80 may control performance of a lead integrity test during the suspected tachyarrhythmia. In some examples, processor 80 may control measurement of an impedance of the lead a plurality of times during the suspected tachyarrhythmia and, in some cases, a plurality of times between consecutive sensed events of the tachyarrhythmia. In general, rapid, intermittent fracture of a lead or disconnection of the lead from an IMD, which may be interpreted by the IMD as a plurality of sensed cardiac events, e.g., R-waves, and lead to detection of a suspected tachyarrhythmia, may also result in variability of impedance measurements of the lead during the suspected tachyarrhythmia. Variability may be particularly evident in impedance measurements made between consecutive sensed events.

In some examples, sensing module 86 and/or processor 80 are capable of collecting, measuring, and/or calculating impedance data for any of a variety of electrical paths that include two or more of electrodes 40, 42, 44, 46, 48, 50, 58, 62, 64 and 66. In the illustrated example, sensing module 86 comprises an impedance measurement module 87, which may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 87, and store measured impedance values in memory 82.

In some examples, processor 80 may perform an impedance measurement by controlling delivery, from signal generator 84, of a voltage pulse between first and second electrodes. Measurement module 87 may measure a resulting current, and processor 80 may calculate a resistance based upon the voltage amplitude of the pulse and the measured amplitude of the resulting current. In other examples, processor 80 may perform an impedance measurement by controlling delivery, from signal generator 84, of a current pulse between first and second electrodes. Measurement module 87 may measure a resulting voltage, and processor 80 may calculate a resistance based upon the current amplitude of the pulse and the measured amplitude of the resulting voltage. Measurement module 87 may include circuitry for measuring amplitudes of resulting currents or voltages, such as sample and hold circuitry.

In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components.

In response to detection a suspected tachyarrhythmia, processor 80 may control a plurality of measurements of the impedance of the sensing configuration that detected the tachyarrhythmia, e.g., the impedance of an electrical path that includes the electrode combination coupled to the detection channel of sensing module 86 that detected the suspected tachyarrhythmia. Impedance measurements for the sensing configuration may indicate whether an integrity issue for the sensing configuration exists, which may have resulted in the detection of the suspected tachyarrhythmia by the sensing configuration. However, in other examples, processor 80 may control a plurality of measurements of the impedance of any one or more electrical paths including combinations of electrodes 40, 42, 44, 46, 48, 50, 58, 62, 64 and 66 in response to detection of a suspected tachyarrhythmia.

According to the instructions stored in memory 82, processor 80 may, in some examples, cause signal generator 84 to deliver multiple test pulses for the plurality of impedance measurements during the suspected tachyarrhythmia. In some examples, a plurality of test pulses is delivered between consecutive sensed events. Processor 80 may control signal generator 84 to deliver the test pulses in a manner to avoid interference with cardiac sensing based on integrity test parameters 83 stored in memory 82. For example, processor 80 may control the timing or amplitude of test pulses based on integrity test parameters 83. Integrity test parameters 83 may, in some examples, specify a period of time, e.g., a window, subsequent a detected event, which may be an R-wave or noise, in which one or more test pulses may be delivered. The duration of the period may be selected to be less than a typical tachyarrhythmia cycle length for patient 16 or patients in general. Furthermore, by controlling the timing of test pulses in this manner, interference with the accuracy of impedance measurements by intrinsic cardiac signals may be avoided.

Processor 80 compares the impedances measured from each of the test pulses, and evaluates the integrity of the sensing configuration based upon the comparison. In some examples, processor 80 determines the variability of the measured impedances. If the impedances vary by greater than an impedance variability threshold 81 stored in memory 82, then processor 80 determines that there is a possible integrity issue with the sensing configuration. Processor 80 may, for example, withhold delivery of any therapeutic stimulation or shock in response to determining that the detection of the suspected tachyarrhythmia may have been due to an integrity issue with the sensing configuration.

Processor 80 may also switch from the current sensing configuration to an alternative sensing configuration in response to determining that the detection of the suspected tachyarrhythmia may have been due to an integrity issue with the sensing configuration. Processor 80 may select the alternative sensing configuration from a list of available sensing configurations stored in memory 82. In some examples, multiple sensing configurations, e.g., electrode combinations, may be tested in response to the detection of the suspected tachyarrhythmia. In such examples, processor 80 may select a tested configuration for which an integrity issue was not indicated as the alternative sensing configuration.

Additionally, processor 80 may change the shock configuration if the integrity test indicates a potential issue with the shock configuration delivering effective therapy to patient 14. For example, if the sensing configuration utilizes one or more electrodes also used to deliver a shock, processor 80 may switch to an alternative shock configuration that no longer includes the one or more electrodes.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, processor 80 may transmit integrity testing information to programmer 24 via telemetry module 88. In some examples, telemetry module 88 may transmit an alert to programmer 24 indicating an integrity issue with the sensing configuration, or programmer 24 may provide such an alert in response to the testing information received from IMD 16. This alert may prompt the user to reprogram IMD 16 to use a different sensing or therapy configuration, or perform some other function to address the possible integrity issue. In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 5:
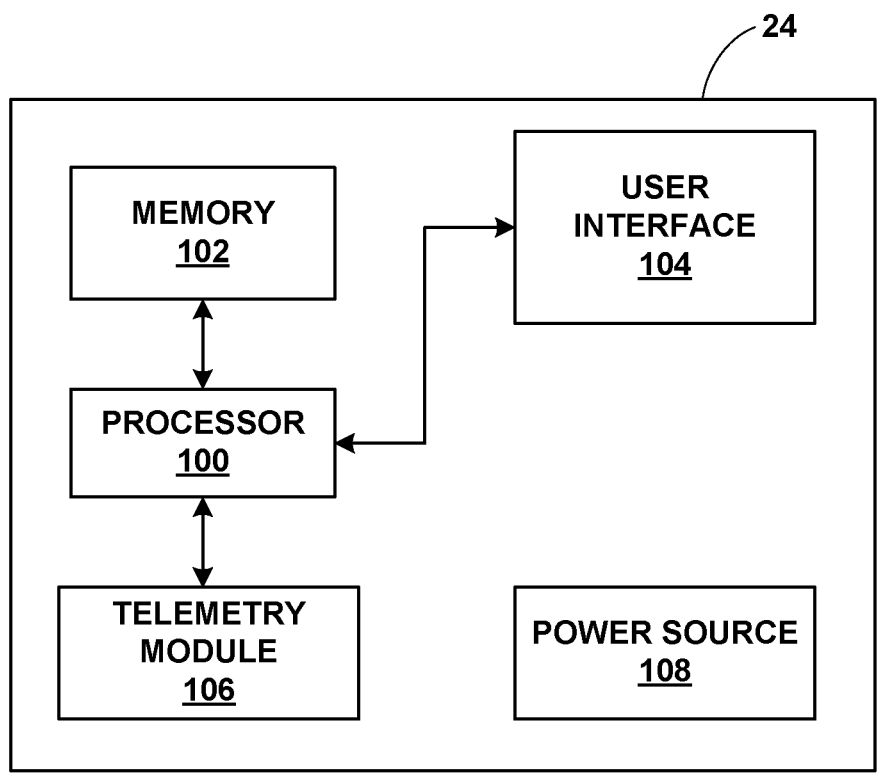
FIG. 5 is a functional block diagram illustrating an example configuration of an external programmer that facilitates user communication with the IMD.

FIG. 5 is functional block diagram illustrating an example configuration of programmer 24. As shown in FIG. 5, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

The user may also use programmer 24 to adjust or control the integrity testing performed by IMD 16. For example, the user may use programmer 24 to program the number of test pulses, the timing of test pulses, the parameters of each test pulse, or any other aspects of the integrity test. In this manner, the user may be able to finely tune the integrity test to the specific condition of patient 14.

In addition, the user may receive an alert from IMD 16 indicating a potential integrity issue with the current sensing configuration via programmer 24. The user may respond to IMD 16 by selecting an alternative sensing configuration via programmer 24. Alternatively, IMD 16 may automatically select an alternative sensing configuration. Programmer 24 may prompt the user to confirm the selection of the alternative sensing configuration.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 102 may be similar to telemetry module 88 of IMD 16 (FIG. 4).

Telemetry module 102 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 100 of programmer 24 and/or one or more processors of one or more networked computers may perform all or a portion of the techniques described herein with respect to processor 80 and IMD 16. For example, processor 100 or another processor may receive voltages or currents measured by IMD 16 to calculate impedance measurements, or may receive impedance measurements from IMD 16. Processor 100 or another processor may compare impedance measurements to evaluate lead integrity using any of the techniques described herein. Processor 100 or another processor may also control IMD 16 to switch sensing or therapy configurations, or may provide an alert, based on the evaluation, according to any of the techniques described herein.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Figure 6:
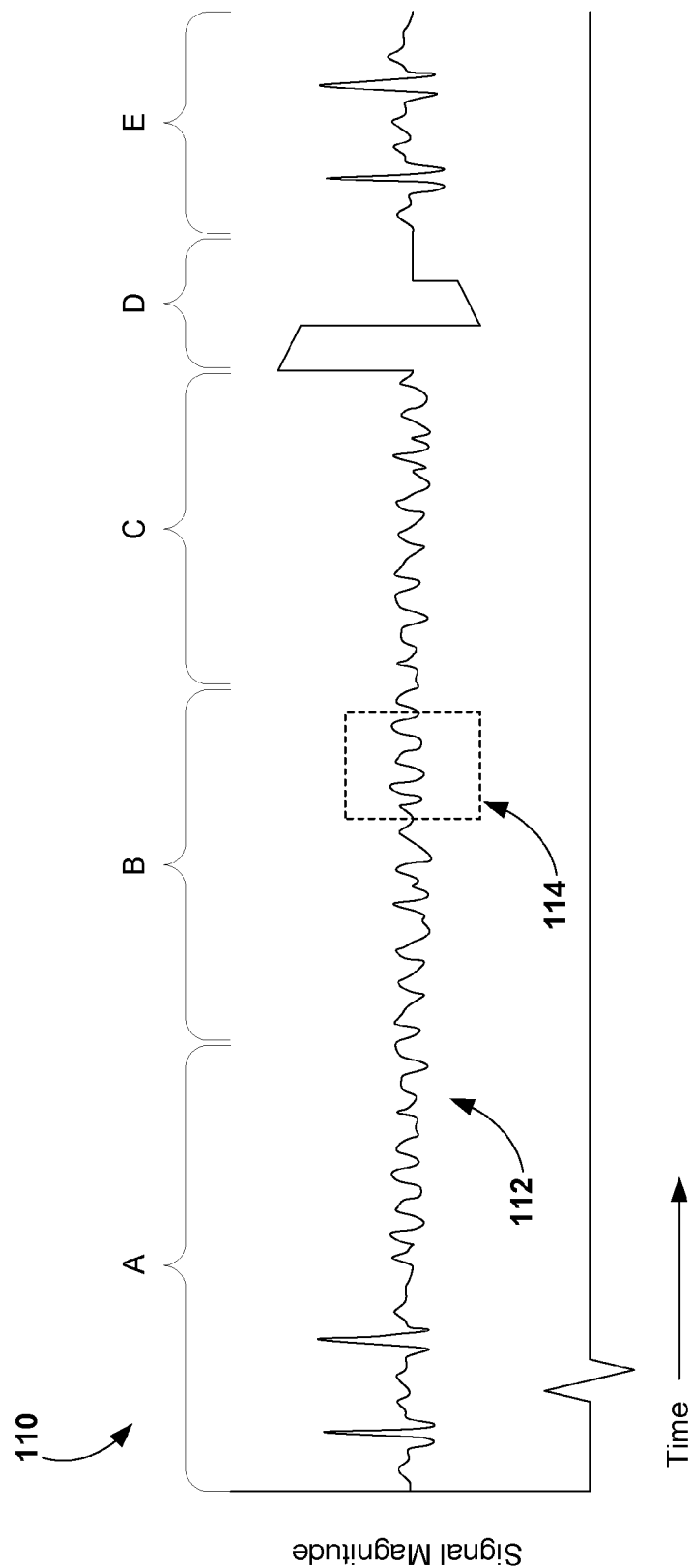
FIG. 6 is a graph illustrating phases of an example cardiac electrogram showing a tachyarrhythmia and a responsive therapeutic shock.

FIG. 6 is an example graph 110 illustrating phases of an example cardiac electrogram 112 showing signs of ventricular fibrillation and a resulting therapeutic shock. Electrogram 112 may correspond to a signal sensed by sensing module 86 via a combination of electrodes 40, 42, 44, 46, 48, 50, 58, 62, 64 and 66, as described above with respect to FIG. 4. However, signal 112 need not be any particular signal analyzed by IMD 16, and is instead used to illustrate activity of the heart, tachyarrhythmia detection, and resulting therapeutic phases. Phases of graph 110 are not to scale and are provided only as an example herein.

Detection phase A illustrates a normal cardiac function at the beginning of signal 112 which develops into a tachyarrhythmia, and more particularly ventricular fibrillation, at the end of detection phase A. During detection phase A, processor 80 monitors signals from the sensing configuration to determine if any tachyarrhythmias occur. The ventricular fibrillation continues for a predetermined amount of time, and processor 80 therefore determines that a ventricular fibrillation occurring. For this reason, signal 112 shows the ventricular fibrillation lasting for a short time before processor 80 exits the detection mode of detection phase A.

After IMD 16 has detected the suspected tachyarrhythmia, IMD 16 enters confirmation phase B where processor 80 confirms that the suspected tachyarrhythmia is indeed occurring from interpretation of signal 112. Confirmation phase B may be of sufficient length to allow processor 80 to detect the tachyarrhythmia a second time. In other embodiments, processor 80 may need to redetect the suspected tachyarrhythmia multiple times before processor 80 can confirm that the tachyarrhythmia is occurring.

Figure 7:
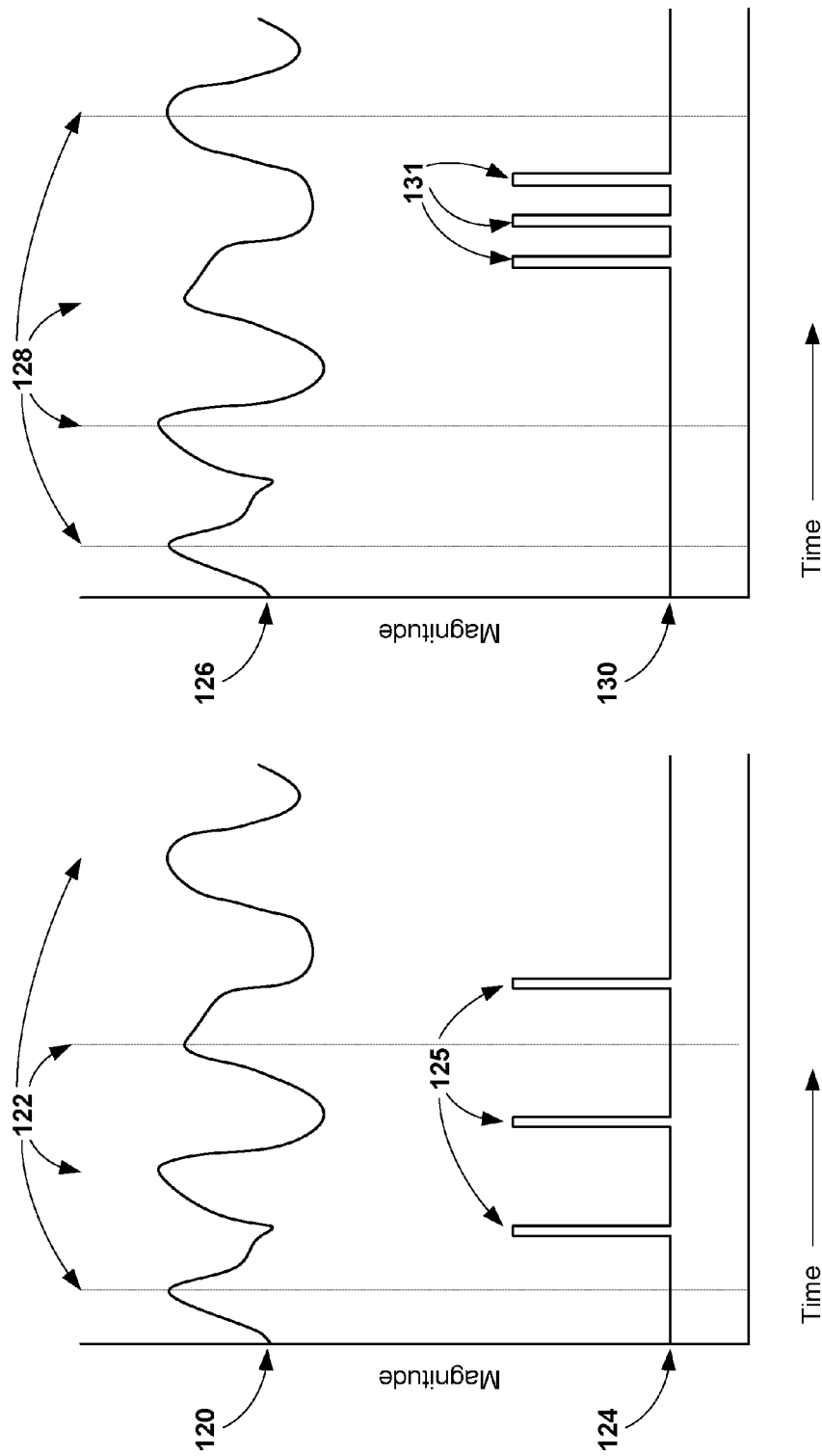
FIGS. 7A and 7B are graphs illustrating examples of delivery of pulses to measure impedance of a lead during a suspected tachyarrhythmia.

Frame 114 indicates when processor 80 performs an integrity test during the suspected tachyarrhythmia, which is further described in FIGS. 7A and 7B. Frame 114 indicates that the integrity test occurs later in confirmation phase B in this example. However, the integrity test may be performed at any time after processor 80 initially detects the suspected tachyarrhythmia. If processor 80 cannot confirm the suspected tachyarrhythmia during confirmation phase B, processor 80 may revert to the normal detection mode of detection phase A. Also, if the integrity test indicates a possible integrity issue with the primary sensing configuration, processor 80 may abort confirmation phase B and reenter detection phase A with an alternative sensing configuration to redetect the suspected tachyarrhythmia if it is occurring. Although the integrity test is performed during confirmation phase B in the example of FIG. 6, the integrity test may be performed at any time during the suspected tachyarrhythmia.

After confirmation phase B is completed by confirming the ventricular fibrillation, processor 80 enters charging phase C. During charging phase C, processor 80 begins charging IMD 16 to provide a therapeutic shock to heart 12. The length of charging phase C may dependent upon the components of IMD 16 and the predetermined stimulation parameters of the shock to be delivered. Processor 80 may still abort therapy during charging phase C, and any stored charge may be depleted slowly according to techniques known in the art.

Once processor 80 exits charging phase C, processor 80 enters shock phase D and delivers the therapeutic shock to heart 12. The shock is shown as a biphasic shock delivered to interrupt the tachycardia event and allow heart 12 to reset and begin normal function once again. In other embodiments, processor 80 may instruct stimulation generator 84 to generate multiple biphasic shocks or monophasic shocks depending on the condition of patient 14 and the user defined therapy.

In the example shown in graph 110, processor exits shock phase D after delivering one biphasic shock and enters redetection phase E. In redetection phase E, processor 80 attempts to detect another tachyarrhythmia if the shock was unsuccessful. The duration of redetection phase E may vary based upon the detected tachyarrhythmia and the amount of time needed to detect further tachyarrhythmias. As shown, signal 112 indicates that normal heart function has recovered, and processor 80 detects the normal function and may exit redetection phase E and enter the normal detection mode of detection phase A. If processor 80 detects that signal 112 still indicates tachycardia, processor 80 may again detect another tachycardia event and enter into another confirmation phase.

In alternative examples, the phases of FIG. 6 may not occur exclusively from one another. For example, processor 80 may operate in confirmation phase B and charging phase C simultaneously to limit the amount of time before therapeutic shock can be delivered. In another example, the confirmation phase B may overlap with detection phase A. In this manner, processor 80 may be able to confirm that a tachyarrhythmia has occurred while processor 80 also determines if any other arrhythmia is occurring in heart 12.

FIGS. 7A and 7B are graphs illustrating examples of delivery of pulses to measure impedance of a lead during a suspected tachyarrhythmia. In FIG. 7A, lines 122 indicate events sensed within signal 120 by sensing module 86 of IMD 16. The sensing of the events is indicated by sensing module 86 to processor 80. The sensed events are events of a suspected tachyarrhythmia detected by processor 80. The events may be actual cardiac events, e.g., R- or fib-waves, or noise.

FIG. 7A also displays test signal 124 that includes a plurality of test pulses 125. Processor 80 controls delivery of test pulses 125 by signal generator 84 during the suspected tachyarrhythmia in order to measure a lead impedance, e.g., of the sensing configuration used by sensing module 86 to detect the suspected tachyarrhythmia, a plurality of times during the suspected tachyarrhythmia. Based upon the impedance measurements from each of multiple test pulses 125, processor 80 evaluates whether there is an integrity problem with one or more leads 18, 20 and 22 and, more particularly, with the sensing configuration used to sense events 122.

In the example illustrated by FIG. 7A, the three test pulses 125 are spaced out between four consecutive sensed events 122. Test pulses 125 are preferably delivered relatively soon after sensing of the events 122 in order to avoid any possible influence of one of test pulses 125 over the sensing of a subsequent event. However, test pulses 125 may be delivered at any time after a sensed event.

Test pulses 125 are generally sub-threshold pulses that cannot induce depolarization of cardiac muscle. For example, each of test pulses 125 may have an amplitude between about 0.2 volts and 0.5 volts, and a pulse width between about 0.1 milliseconds and 0.3 milliseconds. It should be noted that test pulses 125 may be delivered with constant voltage or constant current, depending upon the configuration of IMD 16. Test pulses 125 having these parameters generally are not capable of inducing depolarization, and may not have to be limited to the refractory period of the cardiac cycle, or a portion of the cardiac cycle that avoids the T-wave. Additionally, test pulses 125 having such parameters may be of sufficient magnitude such that an intrinsic cardiac electrical activity does not interfere with the impedance measurement of test pulses 125.

Most preferred test pulses 125 may be those pulses just large enough in magnitude as to not be susceptible to intrinsic signal interference.

Processor 80 compares the measured impedance, as determined based on values received from sensing module 86, for each of test pulses 125 to evaluate whether there is an integrity issue. For example, processor 80 may determine the variability of the measured impedances to determine whether there is an integrity issue. The variability of the impedances measured during a suspected tachyarrhythmia may be determined using any known technique. For example, the variability may be calculated as the variance, standard deviation, or standard error of the impedance measurements. As other examples, the variability may be calculated as the difference between the largest and smallest impedance measurements, or the average of the absolute differences between each measured impedance and the mean of the measured impedances.

Processor 80 may determine that there is an integrity issue if the variability of the measured impedances is greater than a pre-determined impedance variability threshold. The impedance variability threshold may be generally between 10 ohms and 100 ohms, although the impedance threshold may be set outside of this range in some examples. Preferably, the impedance variability threshold may be between 15 ohms and 25 ohms. In other embodiments, the impedance variability threshold may be approximately 20 ohms.

Any number of test pulses may be delivered to acquire any number of impedance measurements during a suspected tachyarrhythmia. In addition, test pulses need not be delivered after consecutive events, and more than one test pulse may be delivered between consecutive events 122. In the example illustrated by FIG. 7B, a test signal 130 includes a plurality of test pulses 131 between consecutive events 128 sensed within signal 126 by sensing module 86. Two, three, or more test pulses may be delivered between consecutive events to acquire two, three or more impedance measurements between the consecutive events. As discussed above, variability due to a lead integrity issue may be particularly evident in impedance measurements made between consecutive sensed events. Processor 80 may determine when to deliver each of test pulses 125, 131 based upon the sensing of events 122, 128.

FIGS. 7A and 7B are presented for purposes of illustration, and are not necessarily drawn to scale. For example, although illustrated in FIGS. 7A and 7B as having similar magnitudes, the magnitude, e.g., voltage magnitude, of test pulses 125, 131 may be significantly greater than the magnitude of sensed events 122, 128. The magnitude of test pulses 125, 131 may be, for example, about ten times greater than the magnitude of sensed events 122, 128.

Figure 8:
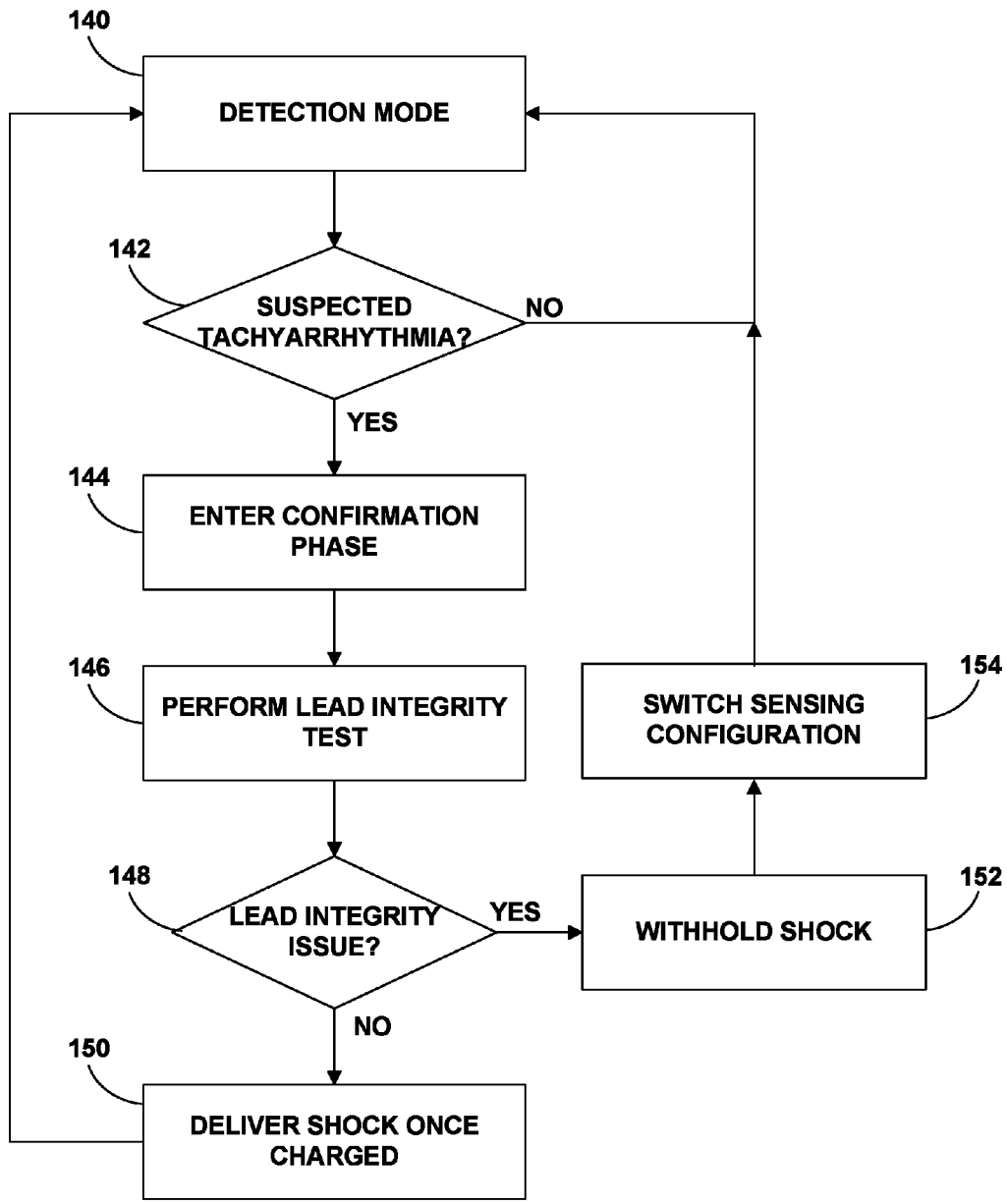
FIG. 8 is a flow diagram illustrating an example method for performing a lead integrity test during a suspected tachyarrhythmia.

FIG. 8 is a flow diagram illustrating an example method for performing a lead integrity test during a suspected tachyarrhythmia. As shown in FIG. 8, processor 80 normally operates in the detection mode to detect tachyarrhythmias with heart 12 (140). If processor 80 does not detect a tachyarrhythmia (142), processor 80 continues in the normal detection mode (140). As mentioned herein, a tachyarrhythmia may include any one of sinus tachycardia, ventricular tachycardia, supraventricular tachycardia, atrial fibrillation, or ventricular fibrillation, as examples.

If processor 80 detects a suspected tachyarrhythmia (142), processor 80 enters the confirmation phase to confirm that that the suspected tachyarrhythmia is occurring (144). Processor 80 then controls performance the integrity test on the current sensing configuration according to the instructions stored in memory 82 (146). The integrity test is performed during the confirmation phase and during the suspected tachyarrhythmia, but other embodiments may perform the pre-shock integrity test at any time during the suspected tachyarrhythmia. Processor 80 uses the integrity test to determine if there is a potential integrity issue with the lead, or, more particularly, the current sensing configuration (148). If the there is no integrity issue (148), processor 80 continues with therapy, charges for the shock, and delivers the therapeutic shock to heart 12 (150).

If there is an integrity issue, e.g., as indicated by suprathreshold variability in impedances from the test pulses (148), processor 80 withholds the shock from being delivered (152). Processor 80 may then control sensing module 86 to switch to an alternative sensing configuration that may effectively detect arrhythmias without the false positives (154). Processor 80 then enters the detection mode to detect tachyarrhythmias (140). If the alternative sensing configuration again detects a suspected tachyarrhythmia, processor 80 repeats the example method described with respect to FIG. 8.

In some examples, processor 80 may withhold the shock if the integrity test indicates a potential integrity issue, and additionally discharge the high voltage capacitors. Alternatively, IMD 16 may hold the charge for the withheld shock for a certain period of time until the alternative sensing configuration has failed to detect another suspected tachyarrhythmia. In other examples, processor 80 may not automatically switch to an alternative sensing configuration. Instead, processor 80 may transmit an alert to programmer 24 or other networked computing device, and request that the user select an alternative sensing configuration for further therapy.

Figure 9:
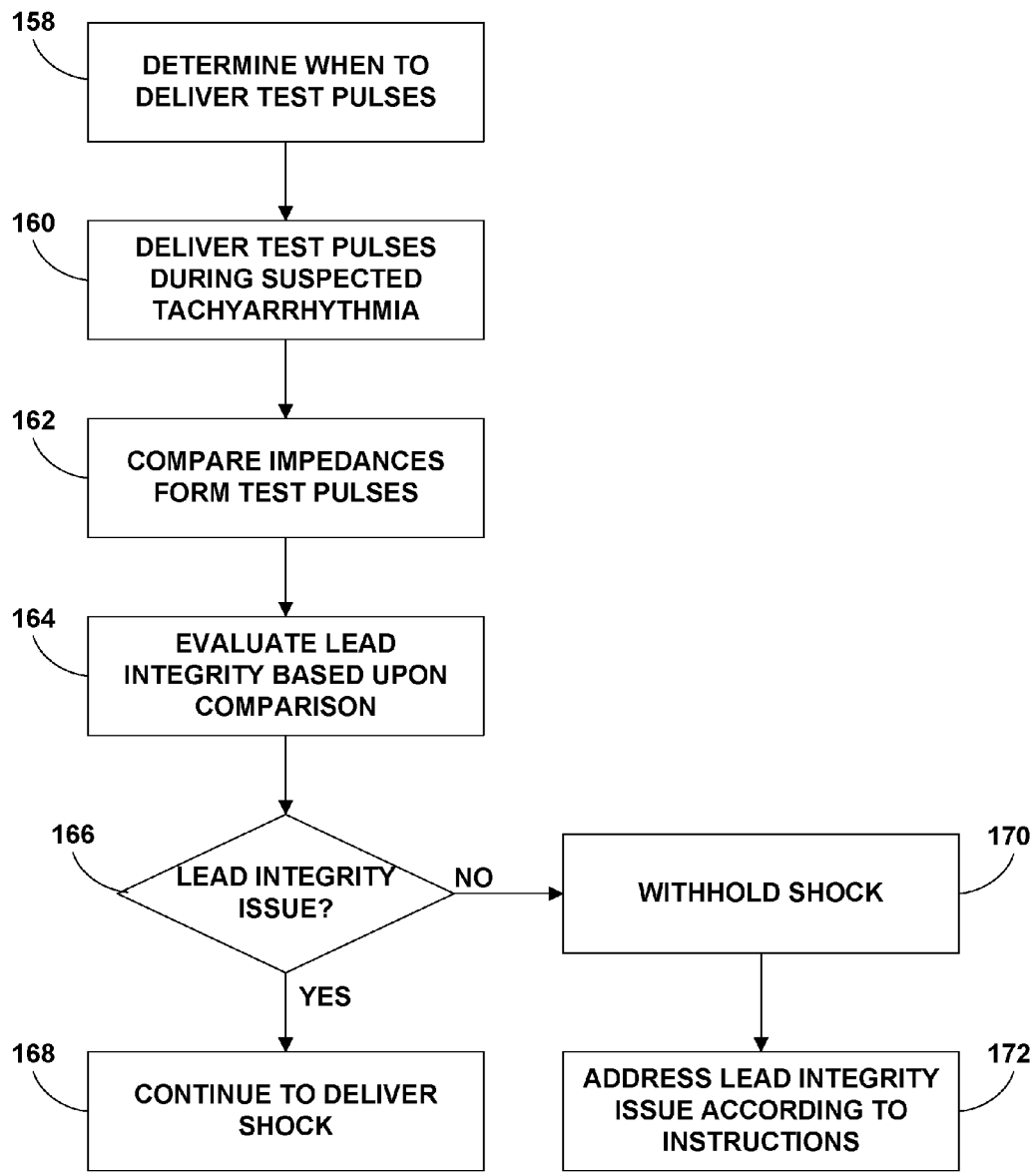
FIG. 9 is a flow diagram illustrating aspects of the example method performing a lead integrity test of FIG. 8 in greater detail.

FIG. 9 is a flow diagram illustrating aspects of the example method of performing a pre-shock lead integrity test of FIG. 8 in greater detail. After a suspected tachyarrhythmia has been detected, processor 80 of IMD 16 performs an integrity test on the sensing configuration that was used to detect the suspected tachyarrhythmia. According to the instructions of memory 82, processor 80 determines when to deliver the multiple test pulses of the integrity test (158). Processor 80 then controls signal generator 84 to deliver the test pulses during the suspected tachyarrhythmia according to the determination (160). As described herein, processor 80 may control delivery of multiple test pulses between consecutive sensed events of the suspected tachyarrhythmia.

Processor 80 measures the impedances from each of test pulses and compares the measured impedances (162). For example, processor 80 may determine the variability of the measured impedances and compare the variability to a threshold, as described herein. Processor 80 then evaluates the integrity of the sensing configuration based upon the variation (164).

If the integrity test does not indicate a potential integrity issue (166), processor 80 continues to deliver the therapeutic shock to heart 12 (168) in response to the suspected tachyarrhythmia. If the integrity test does not indicated a potential integrity issue (166), processor 80 may control signal generator 84 to withhold the shock (170). Processor 80 may then address the potential integrity issue according to the instructions stored within memory 82 (172). Processor 80 may for example, control sensing module 86 to switch to an alternative sensing configuration, alerting the user of the failure via programmer 24, or request patient 14 to confirm that they are feeling certain symptoms before continuing to deliver the shock. The request to patient 14 may be via programmer 24, or via an audible or tactile alert generated from within IMD 16. The patient may respond to the alert by tapping on IMD 16, by placing a magnet proximate to IMD 16, or via programmer 24, as examples.

In some examples, processor 80 also controls measurement of the impedance of the sensing configuration and/or other electrical paths provided by one or more leads prior to detection the suspected tachyarrhythmia. For example, the processor 80 may periodically control measurement of the impedance of one or more electrical paths provided by one or more leads. Processor 80 may control measurement of the impedance one or more times per day, for example, and such measurements may be scheduled to occur at one or more particular times of day. The impedance measurements may be performed using test pulses that are the same as or substantially similar to those used for impedance measurements during a suspected tachyarrhythmia.

In some examples, processor 80 may compare one or more of the impedances measured during a suspected tachyarrhythmia to such non-tachyarrhythmia impedances, and the evaluation of lead integrity may also be based on this comparison. When a lead integrity issue leads to detection of a suspected tachyarrhythmia, one or more impedances measured during the suspected tachyarrhythmia may differ significantly from the non-tachyarrhythmia impedances. Comparing impedances measured during a suspected tachyarrhythmia to at least one non-tachyarrhythmia impedance may include comparing a mean, median or other value derived from impedances measured during a suspected tachyarrhythmia to mean, median or other value derived from non-tachyarrhythmia impedances. To compare impedances measured during a suspected tachyarrhythmia to at least one non-tachyarrhythmia impedance, processor 80 may determine a difference between a tachyarrhythmia and non-tachyarrhythmia impedance, each of which may be a mean, median or other value, as described above, and compare the difference to a threshold.

Furthermore, in some examples, processor 80 (or another processor or device described herein) may determine a threshold for variability of impedance measurements made during a suspected tachyarrhythmia, such as the threshold described above, based on a variability of non-tachyarrhythmia impedances. Accordingly, in some examples, an processor 80 may determine a variability of non-tachyarrhythmia impedances, e.g., measured daily or multiple times per day. The variability may be an overall variability of non-tachyarrhythmia impedances or the variability of the previous N non-tachyarrhythmia impedances. Processor 80 may determine a threshold for variability of impedance measurements made during a suspected tachyarrhythmia by, for example, adding an offset to the variability of the non-tachyarrhythmia impedances. The offset may be, for example, an absolute number or percentage of the variability of the non-tachyarrhythmia impedances.

Figure 10:
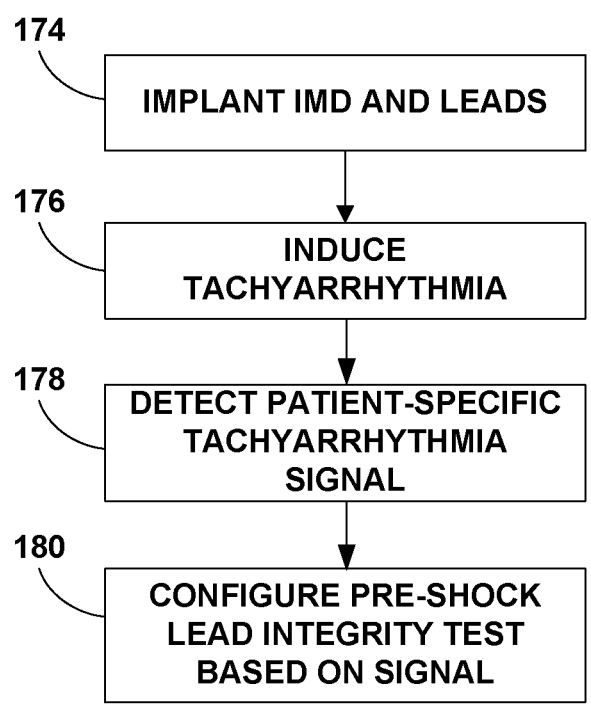
FIG. 10 is a flow diagram illustrating an example method for pre-configuring a pre-shock lead integrity test.

FIG. 10 is a flow diagram illustrating an example method for pre-configuring a pre-shock lead integrity test. In order to treat one or more cardiac conditions of patient 14, a clinician may implant IMD 16 and leads 18, 20, 22 within patient 14 (174). Implantation may include a number of steps to ensure IMD 16 reliability and operability in addition to the functionality of leads 18, 20, 22. For example, the clinician may induce a tachyarrhythmia, e.g., ventricular fibrillation, to ensure that IMD 16 is able to detect the tachycardia under less sensitive settings than that of the normal detection mode (176). This inducement is also used to ensure that IMD 16 delivers appropriate therapy in response to the tachycardia.

In addition to testing IMD 16 therapeutic function, IMD 16 may detect a sample signal from the induced tachyarrhythmia (178). The sample signal may encompass specific characteristics of the intrinsic signals produced by patient 14's heart. For example, the sample signal may include information regarding a typical tachyarrhythmia rate for patient 14.

Processor 80 of IMD 16, processor 100 of programmer 24, another processor of a networked computing device, or a user of any of these devices, may configure the pre-shock lead integrity test for patient 14 based on the sample signal (180). Configuring the integrity test may, for example, include determining the timing of test pulse delivery for impedance measurements, such as determining a start time and duration for a window subsequent to a detected event in which test pulses may be delivered. Amplitude and other information regarding test pulses may also be determined based on the patient-specific tachyarrhythmia signal. Such information may be stored as integrity test parameters 83 in memory 82 of IMD 16, and used by processor 80 to control the performance of integrity tests during suspected tachyarrhythmia.

In other examples, integrity test parameters 83 need not be determined based on a sample signal from patient 14. Instead, integrity test parameters 83 may be derived based on observations made with respect to multiple other patients. For example, test-pulse timing information may be determined based on a typical fibrillation rate across a class of patients.

Figure 11:
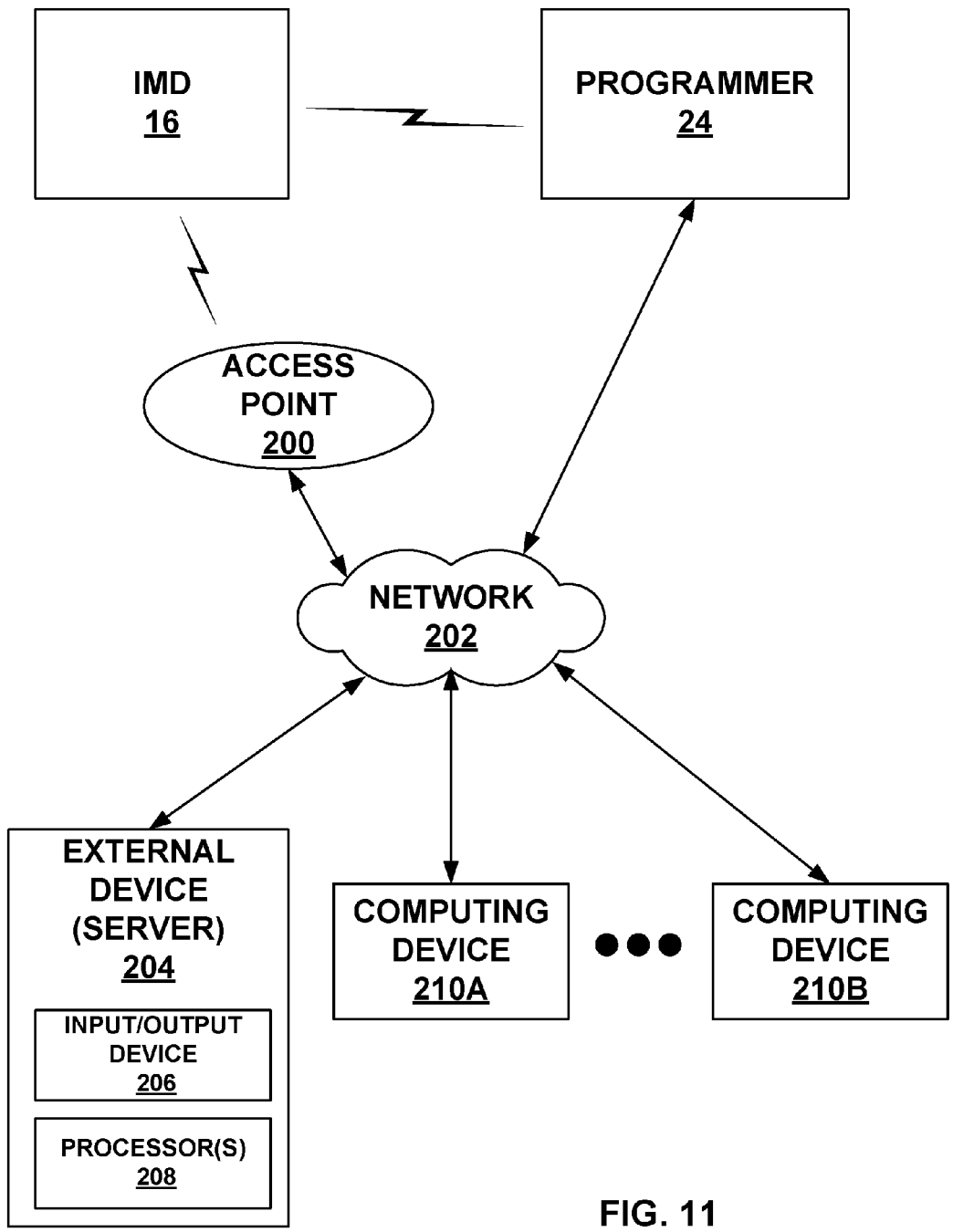
FIG. 11 is a block diagram illustrating an example system that includes an external device, such as a server, and one or more computing devices that are coupled to the IMD and programmer shown in FIG. 1 via a network.

FIG. 11 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 11, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 186 via any of a variety of connections, such as telephone dial-up, digital subscriber line (DSL), or cable modem connections. In other embodiments, access point 200 may be coupled to network 130 through different forms of connections, including wired or wireless connections. In some embodiments, access point 128 may be co-located with patient 14 and may comprise one or more programming units and/or computing devices (e.g., one or more monitoring units) that may perform various functions and operations described herein. For example, access point 128 may include a home-monitoring unit that is co-located with patient 14 and that may monitor the activity of IMD 16. In some embodiments, server 204 or computing devices 210 may perform any of the various functions or operations described herein.

In some cases, server 182 may be configured to provide a secure storage site for archival of sensing integrity information that has been collected from IMD 16 and/or programmer 24. Network 186 may comprise a local area network, wide area network, or global network, such as the Internet. In some cases, programmer 24 or server 182 may assemble sensing integrity information in web pages or other documents for viewing by and trained professionals, such as clinicians, via viewing terminals associated with computing devices 184A-184N. System 180 may be implemented, in some aspects, with general network technology and functionality similar to that provided by the Medtronic CareLink® Network developed by Medtronic, Inc., of Minneapolis, Minn.

Various examples have been described. These and other examples are within the scope of the following claims. For example, although pre-shock integrity testing is directed herein toward cardiac therapy, this disclosure may also be applicable to other therapies in which pre-therapy lead integrity testing may be appropriate. These therapies may include spinal cord stimulation, deep brain stimulation, pelvic floor stimulation, gastric stimulation, occipital stimulation, functional electrical stimulation, and any other stimulation therapy utilizing electrode sensing methods.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
    detecting a suspected tachyarrhythmia via at least one implantable medical lead;
    in response to detecting the suspected tachyarrhythmia, measuring an impedance of the lead a plurality of times during the suspected tachyarrhythmia to obtain a plurality of impedance measurements, wherein measuring an impedance of the lead a plurality of times during the suspected tachyarrhythmia comprises:
        delivering a plurality of test pulses via the lead, wherein delivering the plurality of test pulses comprises controlling a timing of the pulses to avoid interference with electrical sensing of cardiac events, and measuring a respective one of the plurality of impedance measurements based on delivery of each of the plurality of test pulses;
    comparing the impedance measurements; and
    evaluating integrity of the lead based upon the comparison.

2. The method of claim 1,
    wherein the suspected tachyarrhythmia comprises a plurality of sensed events,
    wherein controlling the timing of the pulses comprises delivering the pulses during a period subsequent to one of the sensed events, and
    wherein a duration of the period is predetermined based on a previously measured tachyarrhythmia rate of a patient in which the lead is implanted or at least one other patient.

3. The method of claim 1, further comprising at least one of providing an alert to a user based on the evaluation or withholding delivery of a responsive therapeutic shock for the suspected tachyarrhythmia based on the evaluation.

4. A method comprising:
    detecting a suspected tachyarrhythmia via at least one implantable medical lead;
    in response to detecting the suspected tachyarrhythmia, measuring an impedance of the lead a plurality of times during the suspected tachyarrhythmia to obtain a plurality of impedance measurements;
    comparing the impedance measurements; and
    evaluating integrity of the lead based upon the comparison,
    wherein comparing the impedance measurements comprises determining a variability of the impedance measurements, and
    wherein evaluating lead integrity comprises evaluating lead integrity based on the variability.

5. The method of claim 4, wherein the plurality of impedance measurements comprises a plurality of suspected tachyarrhythmia impedance measurements, the method further comprising:
    measuring the impedance of the lead a plurality of times prior to the detection of the suspected tachyarrhythmia to obtain a plurality of non-tachyarrhythmia impedance measurements;
    determining a variability of the non-tachyarrhythmia impedance measurements; and
    determining a tachyarrhythmia impedance measurement variability threshold based on the variability of the non-tachyarrhythmia impedance measurements, and
    wherein evaluating lead integrity based on the variability comprises comparing the variability of the suspected tachyarrhythmia impedance measurements the tachyarrhythmia impedance measurement variability threshold.

6. A method comprising:
    detecting a suspected tachyarrhythmia via at least one implantable medical lead;
    in response to detecting the suspected tachyarrhythmia, measuring an impedance of the lead a plurality of times during the suspected tachyarrhythmia to obtain a plurality of impedance measurements, wherein the plurality of impedance measurements comprises a plurality of suspected tachyarrhythmia impedance measurements;
    comparing the impedance measurements;

evaluating integrity of the lead based upon the comparison;
measuring the impedance of the lead at least once prior to the detection of the suspected tachyarrhythmia to obtain at least one non-tachyarrhythmia impedance measurement; and
comparing the suspected tachyarrhythmia impedance measurements to the non-tachyarrhythmia impedance measurement,
wherein evaluating the integrity of the lead further comprises evaluating the integrity of the lead based on the comparison of the suspected tachyarrhythmia impedance measurements to the non-tachyarrhythmia impedance measurement.

7. A method comprising:
detecting a suspected tachyarrhythmia via at least one implantable medical lead;
in response to detecting the suspected tachyarrhythmia, measuring an impedance of the lead a plurality of times during the suspected tachyarrhythmia to obtain a plurality of impedance measurements;
comparing the impedance measurements;
evaluating integrity of the lead based upon the comparison; and
switching to an alternative electrode combination for at least one of sensing of cardiac events or delivery of stimulation based on the evaluation.

8. A system comprising:
an implantable medical lead;
an implantable medical device (IMD) coupled to the lead, wherein the IMD detects a suspected tachyarrhythmia via the lead, measures, in response to detecting the suspected tachyarrhythmia, an impedance of the lead a plurality of times during the suspected tachyarrhythmia, delivers a plurality of test pulses via the lead, controls a timing of the pulses to avoid interference with electrical sensing of cardiac events, and measures a respective one of the plurality of impedance measurements based on delivery of each of the plurality of test pulses; and
a processor that compares the measured impedances, and evaluates integrity of the lead based upon the comparison.

9. The system of claim 8,
wherein the suspected tachyarrhythmia comprises a plurality of sensed events,
wherein the IMD delivers the pulses during a period subsequent to one of the sensed events, and
wherein a duration of the period is predetermined based on a previously measured tachyarrhythmia rate of a patient in which the lead is implanted or at least one other patient.

10. The system of claim 8, wherein the processor performs one of providing an alert to a user based on the evaluation or controlling the IMD to withhold delivery of a responsive therapeutic shock for the suspected tachyarrhythmia based on the evaluation.

11. The system of claim 8, wherein the processor comprises a processor of the IMD.

12. A system comprising:
an implantable medical lead;
an implantable medical device (IMD) coupled to the lead, wherein the IMD detects a suspected tachyarrhythmia via the lead and, in response to detecting the suspected tachyarrhythmia, measures an impedance of the lead a plurality of times during the suspected tachyarrhythmia; and
a processor that compares the measured impedances, and evaluates integrity of the lead based upon the comparison, wherein the processor determines a variability of the impedance measurements, and evaluates lead integrity based on the variability.

13. The system of claim 12,
wherein the plurality of impedance measurements comprises a plurality of suspected tachyarrhythmia impedance measurements,
wherein the IMD measures the impedance of the lead a plurality of times prior to the detection of the suspected tachyarrhythmia to obtain a plurality of non-tachyarrhythmia impedance measurements, and
wherein the processor determines a variability of the non-tachyarrhythmia impedance measurements, determines a tachyarrhythmia impedance measurement variability threshold based on the variability of the non-tachyarrhythmia impedance measurements, and compares the variability of the suspected tachyarrhythmia impedance measurements the tachyarrhythmia impedance measurement variability threshold to evaluate the integrity of the lead.

14. A system comprising:
an implantable medical lead;
an implantable medical device (IMD) coupled to the lead, wherein the IMD detects a suspected tachyarrhythmia via the lead and, in response to detecting the suspected tachyarrhythmia, measures an impedance of the lead a plurality of times during the suspected tachyarrhythmia; and
a processor that compares the measured impedances, and evaluates integrity of the lead based upon the comparison,
wherein the plurality of impedance measurements comprises a plurality of suspected tachyarrhythmia impedance measurements,
wherein the IMD measures the impedance of the lead at least once prior to the detection of the suspected tachyarrhythmia to obtain at least one non-tachyarrhythmia impedance measurement, and
wherein the processor compares the suspected tachyarrhythmia impedance measurements to the non-tachyarrhythmia impedance measurement, and evaluates the integrity of the lead based on the comparison of the suspected tachyarrhythmia impedance measurements to the non-tachyarrhythmia impedance measurement.

15. A system comprising:
an implantable medical lead;
an implantable medical device (IMD) coupled to the lead, wherein the IMD detects a suspected tachyarrhythmia via the lead and, in response to detecting the suspected tachyarrhythmia, measures an impedance of the lead a plurality of times during the suspected tachyarrhythmia; and
a processor that compares the measured impedances, and evaluates integrity of the lead based upon the comparison, wherein the processor controls the IMD to switch to an alternative electrode combination for at least one of sensing of cardiac events or delivery of stimulation based on the evaluation.

* * * * *